US005681747A

United States Patent [19]

Boggs et al.

[11] Patent Number: 5,681,747
[45] Date of Patent: Oct. 28, 1997

[54] NUCLEIC ACID SEQUENCES ENCODING PROTEIN KINASE C AND ANTISENSE INHIBITION OF EXPRESSION THEREOF

[75] Inventors: Russell T. Boggs; Nicholas M. Dean, both of Cardiff-by-the-Sea, Calif.

[73] Assignee: ISIS Pharmaceuticals, Inc., Carlsbad, Calif.

[21] Appl. No.: 199,779

[22] Filed: Feb. 22, 1994

Related U.S. Application Data

[63] Continuation-in-part of Ser. No. 89,996, Jul. 9, 1993, which is a continuation-in-part of Ser. No. 852,852, Mar. 16, 1992, abandoned.

[51] Int. Cl.$^6$ .............................. C12N 15/63; C12N 5/00; C07H 21/04
[52] U.S. Cl. ..................... 435/375; 435/375; 435/69.7; 435/172.3; 435/6; 935/62; 935/34; 935/70; 536/24.2
[58] Field of Search ........................... 435/69.7, 199, 435/240.2, 6, 172.3; 536/24.1, 24.2, 24.3, 24.33, 23.1, 23.4, 24.5; 514/44

[56] References Cited

U.S. PATENT DOCUMENTS 5,034,506  7/1991  Summerton et al. ........................ 528/391

FOREIGN PATENT DOCUMENTS

WO 93/13121  7/1993  WIPO.

OTHER PUBLICATIONS

Bories, D. et al. Down-Regulation of a Serine Protease, Myelobastin, Causes Growth Arrest and Differentiation of Promyelocytic Leukemia Cells. Cell, vol. 59, 959–968, Dec. 22, 1989.
Sulston, J. et al. The C. elegans genome sequencing project: a beginning. Nature, vol. 356, 37–41, Mar. 5, 1992.
Crooke, S.T. et al. Antisense Research and Applications. CRC Press, 7–35, 1993.
Uhlmann, E. et al. Antisense Oligonucleotides: A New Therapeutic Principle. Chemical Reviews, 90 (4), 544–584, Jun. 1960.
Van Der Straeten, D et al. Plant Enolase: Gene Structure, Expression, and Evolution. Plant Cell, vol. 3, 719–735, Jul. 1991.
Standaert, M. et al. Protein Kinase C Antisense DNA and PKC Pseudosubstrate Inhibit Insulin–Stimulated 2–Deoxyglucose Uptake in Rat Adipocytes. J. of Cellular Biochemistry. Keystone symposia on Molecular & Cellular Biology, Suppl 15B, Jan. 18, 1991.
Finkenzeller, G. et al. Sequence of Human Protein Kinase C alpha. Nucleic Acids Research, vol. 18, No. 8, 2183, 1990.
Wallner BP. et al. Cloning and expression of human lipocortin, a phopholipase A2 inhibitor with potential anti–inflammatory activity. Nature, vol. 320, 77–81, Mar. 6, 1986.
Borek et al., "Long–Chain (Sphingoid) Bases Inhibit Multistage Carcinogenesis in Mouse C3H/10T1/2 Cells Treated with Radiation and Phorbol 12–Myristate 13–Acetate", Proc. Natl. Acad. Sci . 88:1953–1957 (1991).
Endo et al., "Cell Membrane Signaling as Target in Cancer Therapy: Inhibitory Effect of N,N–Dimethyl and N,N,N–Trimethyl Sphingosine Derivatives on In Vitro and In Vivo Growth of Human Tumor Cells in Nude Mice", Cancer Research 51:1613–1618 (1991).
Gescher, A. and Dale, I.L., "Protein KinaseC–A Novel Target for Rational Anti–Cancer Drug Design?" Anti–Cancer Drug Design 4:93–105 (1989).
Hegemann, L. and G. Mahrle, "Chapter 22: Biochemical Pharmacology of Protein Kinase C and Its Relevance for Dermatology", Pharmacology of the Skin, H. Mukhtar, ed., pp. 357–368, CRC Press, Boca Raton, FL, (1992).
Hidaka and Hagiwara, "Pharmacology of the Isoquinoline Sulfonamide Protein Kinase C Inhibitors", Trends in Pharm. Sci. 8:162–164 (1987).
Nielsen et al., "Sequence–Selective Recognition of DNA by Strand Displacement with a Thymine–Substituted Polyamide", Science 254:1497–1500 (1991).
Parker et al., "The Complete Primary Structure of Protein Kinase C—The Major Phorbol Ester Receptor", Science 233:853–866 (1986).
Sakanoue et al., "Protein Kinase C Acitivity as Marker for Colorectal Cancer", Int. J. Cancer 48:803–806 (1991).
Weinstein, "Cancer Prevention: Recent Progress and Future Opportunities", Cancer Res. (Suppl.) 51:5080s–5085s (1991).

Primary Examiner—Jasemine C. Chambers
Assistant Examiner—Karen M. Hauda
Attorney, Agent, or Firm—Woodcock Washburn Kurtz Mackiewicz & Norris LLP

[57] ABSTRACT

New nucleic acid sequences are provided which encode 3' untranslated regions of human protein kinase Cα. Compositions and methods are provided for the treatment and diagnosis of diseases associated with protein kinase Cα. Oligonucleotides are provided which are specifically hybridizable with nucleic acid encoding PKCα. Methods of treating animals suffering from disease amenable to therapeutic intervention by modulating protein kinase C expression with an oligonucleotide specifically hybridizable with RNA or DNA corresponding to PKC are disclosed. Polynucleotide probes for PKCα are also disclosed.

14 Claims, 2 Drawing Sheets

Figure 1

```
TGATCAACTG TTCAGGGTCT CTCTCTTACA ACCAAGAACA TTATCTTAGT      50
GGAAGATGGT ACGTCATGCT CAGTGTCCAG TTTAATTCTG TAGAAGTTAC     100
GTCTGGCTCT AGGTTAACCC TTCCTAGAAA GCAAGCAGAC TGTTGCCCCA     150
TTTTGGGTAC AATTTGATAT ACTTTCCATA CCCTCCATCT GTGGATTTTT     200
CAGCATTGGA ATCCCCCAAC CAGAGATGTT AAAGTGAGCT GTCCCAGGAA     250
ACATCTCCAC CCAAGACGTC TTTGGAATCC AAGAACAGGA AGCCAAGAGA     300
GTGAGCAGGG AGGGATTGGG GGTGGGGGGA GGCCTCAAAA TACCGACTGC     350
GTCCATTCTC TGCCTCCATG GAAACAGCCC CTAGAATCTG AAAGGCCGGG     400
ATAAACCTAA TCACTGTTCC CAAACATTGA CAAATCCTAA CCCAACCATG     450
GTCCAGCAGT TACCAGTTTA AACAAAAAAA ACCTCAGATG AGTGTTGGGT     500
GAATCTGTCA TCTGGTACCC TCCTTGGTTG ATAACTGTCT TGATACTTTT     550
CATTCTTTGT AAGAGGCCAA ATCGTCTAAG GACGTTGCTG AACAAGCGTG     600
TGAAATCATT TCAGATCAAG GATAAGCCAG TGTGTACATA TGTTCATTTT     650
AATCTCTGGG AGATTATTTT TCCATCCAGG GTGCCATCAG TAATCATGCC     700
ACTACTCACC AGTGTTGTTC GCCAACACCC ACCCCACAC ACACCAACAT      750
TTTGCTGCCT ACCTTGTTAT CCTTCTCAAG AAGCTGAAGT GTACGCCCTC     800
TCCCCTTTTG TGCTTATTTA TTTAATAGGC TGCAGTGTCG CTTATGAAAG     850
TACGATGTAC AGTAACTTAA TGGAAGTGCT GACTCTAGCA TCAGCCTCTA     900
CCGATTGATT TTCCTCCCTT CTCTAGCCCT GGATGTCCAC TTAGGGATAA     950
AAAGAATATG GTTTTGGTTC CCATTTCTAG TTCACGTTGA ATGACAGGCC    1000
TGGAGCTGTA GAATCAGGAA ACCCGGATGC CTAACAGCTC AAAGATGTTT    1050
TGTTAATAGA AGGATTTTAA TACGTTTTGC AAATGCATCA TGCAATGAAT    1100
TTTGCATGTT TATAATAAAC CTTAATAACA AGTGAATAGA AGGATTTTAA    1150
TACGTTTTGC AAATGCATCA TGCAATGAAT TTTGCATGTT TATAATAAAC    1200
CTTAATAACA AGTGAATCTA TATTATTGAT ATAATCGTAT CAAGTATAAA    1250
GAGAGTATTA TAATAATTTT ATAAGACACA ATTGTGCTCT ATTTGTGCAG    1300
GTTCTTGTTT CTAATCCTCT TTTCTAATTA AGTTTTAGCT GAATCCCTTG    1350
CTTCTGTGCT TTCCCTCCCT GCACATGGGC ACTGTATCAG ATAGATTACT    1400
TTTTAAATGT AGATAAAATT TCAAAAATGA ATGGCTAGTT TACGTGATAG    1450
ATTAGGCTCT TACTACATAT GTGTGTGTAT ATATATGTAT TTGATTCTAC    1500
CTGCAAACAA ATTTTTATTG GTGAGGACTA TTTTTGAGCT GACACTCCCT    1550
CTTAGTTTCT TCATGTCACC TTTCGTCCTG GTTCCTCCGC CACTCTTCCT    1600
CTTGGGGACA ACAGGAAGTG TCTGATTCCA GTCTGGCCTA GTACGTTGGT    1650
ACACACGTGG CATTGCGCAG CACCTGGGCT GACCTTTGTG TGTAGCGTGT    1700
GTGTGTGTTT CCTTCTTCCC TTCAGCCTGT GACTGTTGCT GACTCCAGGG    1750
GTGGGAGGGA TGGGGAGACT CCCCTCTTGC TGTGTGTACT GGACACGCAG    1800
GAAGCATGCT GA                                             1812
```

NUCLEIC ACID SEQUENCES ENCODING PROTEIN KINASE C AND ANTISENSE INHIBITION OF EXPRESSION THEREOF

CROSS REFERENCE TO RELATED APPLICATIONS

This application is a continuation-in-part of Ser. No. 089,996 filed Jul. 9, 1993, which is a continuation in part of Ser. No. 852,852, now abandoned, filed Mar. 16, 1992.

FIELD OF THE INVENTION

This invention relates to novel nucleic acid sequences which encode protein kinase C and to polynucleotide probes for such sequences. This invention also relates to therapies, diagnostics, and research reagents for conditions which are associated with the expression of protein kinase C. In particular, this invention relates to antisense oligonucleotides specifically hybridizable with nucleic acids relating to protein kinase C. These oligonucleotides have been found to modulate the expression of protein kinase C.

BACKGROUND OF THE INVENTION

The phosphorylation of proteins plays a key role in the transduction of extracellular signals into the cell. Enzymes, called kinases, which effect such phosphorylations are targets for the action of growth factors, hormones, and other agents involved in cellular metabolism, proliferation and differentiation. One of the major signal transduction pathways involves the enzyme protein kinase C (PKC), which is known to have a critical influence on cell proliferation and differentiation. PKC is activated by diacylglycerols (DAGs), which are metabolites released in signal transduction.

Interest in PKC was stimulated by the finding that PKC is the major, and perhaps only, cellular receptor through which a class of tumor-promoting agents called phorbol esters exert their pleiotropic effects on cells [Gescher et al., *Anti-Cancer Drug Design* 4:93–105 (1989)]. Phorbols capable of promoting tumor growth can mimic the effect of DAG in activating PKC, suggesting that these tumor promoters act through PKC and that activation of this enzyme is at least partially responsible for the resulting tumorigenesis [Parker et al., *Science* 233:853–866 (1986)].

Experimental evidence indicates that PKC plays a role in tumor growth in colon cancer. It is believed that specific bacteria in the intestinal tract convert lipids to DAG, thus activating PKC and altering cell proliferation. This may explain the correlation between high dietary fat and colon cancer [Weinstein, *Cancer Res.* (*Suppl.*) 51:5080s–5085s (1991)]. It has also been demonstrated that a greater proportion of the PKC in the colonic mucosa of patients with colorectal cancer is in an activated state compared to that of patients without cancer [Sakanoue et al., *Int. J. Cancer* 48:803–806 (1991)]. Increased tumorigenicity is also correlated with overexpression of PKC; cultured cells which overexpress PKC cause increased tumorgenicity in nude mice when the cells were innoculated in the mice. A mutant form of PKC induces highly malignant tumor cells with increased metastatic potential.

Sphingosine and related inhibitors of PKC activity have been shown to inhibit tumor cell growth and radiation-induced transformation in vivo [Endo et al., *Cancer Research* 51:1613–1618 (1991); Borek et al., *Proc. Natl. Acad. Sci.* 88:1953–1957 (1991)]. A number of experimental or clinically useful anti-cancer drugs show modulatory effects on PKC. Therefore, inhibitors of PKC may be important cancer-preventive or therapeutic agents. PKC has been suggested as a plausible target for rational design of conventional anti-cancer drugs [Gescher, A. and Dale, I. L., *Anti-Cancer Drug Design,* 4:93–105 (1989)].

Experiments also indicate that PKC plays an important role in the pathophysiology of hyperproliferative skin disorders such as psoriasis and skin cancer. Psoriasis is characterized by inflammation, hyperproliferation of the epidermis and decreased differentiation of cells. Various studies implicate PKC in the cause of these symptoms. PKC stimulation in cultured keratinocytes can be shown to cause hyperproliferation. Furthermore, inflammation can be induced by phorbol esters which is regulated by PKC. DAG is also implicated in the involvement of PKC in dermatological diseases, and is formed to an increased extent in psoriatic lesions.

Inhibitors of PKC have been shown to have both antiproliferative and antiinflammatory effects in vitro. Some antipsoriasis drugs, such as cyclosporine A and anthralin, have been shown to inhibit PKC. Inhibition of PKC has been suggested as a therapeutic approach to the treatment of psoriasis [Hegemann, L. and G. Mahrle, *Pharmacology of the Skin*, H. Mukhtar, ed., p. 357–368, CRC Press, Boca Raton, Fla., 1992].

PKC is not a single enzyme, but a family of enzymes. It is presently believed that different PKC isozymes may be involved in various disease processes depending on the organ or tissue in which they are expressed. For example, in psoriatic lesions there is an alteration in the ratio between PKC-α and PKC-β, with preferential loss of PKC-β compared to normal skin [Hegemann, L. and G. Mahrle, *Pharmacology of the Skin, H. Mukhtar, ed., p. 357–368,* CRC Press, Boca Raton, Fla., 1992].

Even for a given isozyme, there may be multiple RNA transcripts expressed from a single gene. In the case of PKCα, for example, two mRNA transcripts are seen: a long (approximately 8.5 kb) transcript and a short (approximately 4 kb) transcript. Multiple PKCα transcripts are produced from the murine and the bovine PKCα genes as well. The ratio between the long and short transcripts varies between species and is believed to vary between tissues as well. In addition, there may be some correlation between this ratio and the proliferative state of cells.

Although numerous compounds have been identified as PKC inhibitors (see Hidaka and Hagiwara, *Trends in Pharm. Sci.* 8:162–164 (1987) for review), few have been found which inhibit PKC specifically. While the quinoline sulfonamide derivatives such as 1-(5-isoquinolinesulfonyl)-2-methylpiperazine (H-7) inhibit PKC at micromolar concentrations, they exhibit similar enzyme inhibition kinetics for PKC and the CAMP-dependent and cGMP-dependent protein kinases. Staurosporine, an alkaloid product of Streptomyces sp., and its analogs, are the most potent in vitro inhibitors of PKC identified to date. However, they exhibit only limited selectivity among different protein kinases [Gescher, *Anti-Cancer Drug Design* 4:93–105 (1989)]. Certain ceramides and sphingosine derivatives have been shown to have PKC inhibitory activity and to have promise for therapeutic uses, however, there remains a long-felt need for specific inhibitors of the enzymes.

There is also a desire to inhibit specific PKC isozymes, both as a research tool and as treatment for diseases which may be associated with particular isozymes. Godson et al. [*J. Biol. Chem.* 268:11946–11950 (1993)]recently disclosed use of stable transfection of antisense PKC-α cDNA in cytomegalovirus promotor-based expression vectors to specifically decrease expression of PKC-α protein by approximately 70%. It was demonstrated that this inhibition causes a loss of phospholipase $A_2$-mediated arachidonic acid release in response to the phorbol ester PMA. Attempts by the same researchers at inhibiting PKC activity with oligodeoxynucleotides were ultimately unsuccessful. Thus, it is desireable to identify methods of modulating PKC and to develop therapeutic, diagnostic, and research reagents related thereto.

OBJECTS OF THE INVENTION

It is an object of the invention to provide novel nucleic acid molecules encoding a 3'-untranslated region of human PKCα, including sequences unique to the long mRNA transcript of PKCα.

It is a further object of the invention to provide antisense oligonucleotides which are capable of modulating the expression of PKCα.

Another object of the invention is to provide antisense oligonucleotides which are capable of selectively modulating the expression of particular mRNA transcripts of PKCα.

A further object of the invention is to provide polynucleotide probes for detection of human PKCα.

A still further object of the invention is to provide polynucleotide probes for detection of particular mRNA transcripts of PKCα.

Yet another object is to provide means for diagnosis of diseases associated with PKCα.

A further object of the invention is to provide means for differential diagnosis of diseases associated with particular mRNA transcripts of PKCα.

It is an object of the invention to provide therapies for neoplastic, hyperproliferative, inflammatory and other disease states associated with PKCα.

Another object of the invention is to provide selective therapies for diseases associated with particular mRNA transcripts of PKCα.

A still further object of the invention is to provide research tools for the study of the effects of PKCα expression and diseases associated therewith.

An additional object of the invention is to provide research tools for the study of the effects of expression of particular transcripts of PKCα and diseases associated therewith.

These and other objects of this invention will become apparent from a review of the instant specification.

BRIEF DESCRIPTION OF THE DRAWINGS

FIG. 1 is a nucleotide sequence (SEQ ID NO: 1) of a portion of the 3' untranslated region of the human PKCα gene beginning at the Bcl I site near the 3' end of the previously known sequence and extending in the 3' direction. Newly determined sequences begin at nucleotide 56 and are underlined (SEQ ID NO:2). Bold sequences are unique to the long mRNA transcript of PKCα (SEQ ID NO:3).

SUMMARY OF THE INVENTION

Figure 2:
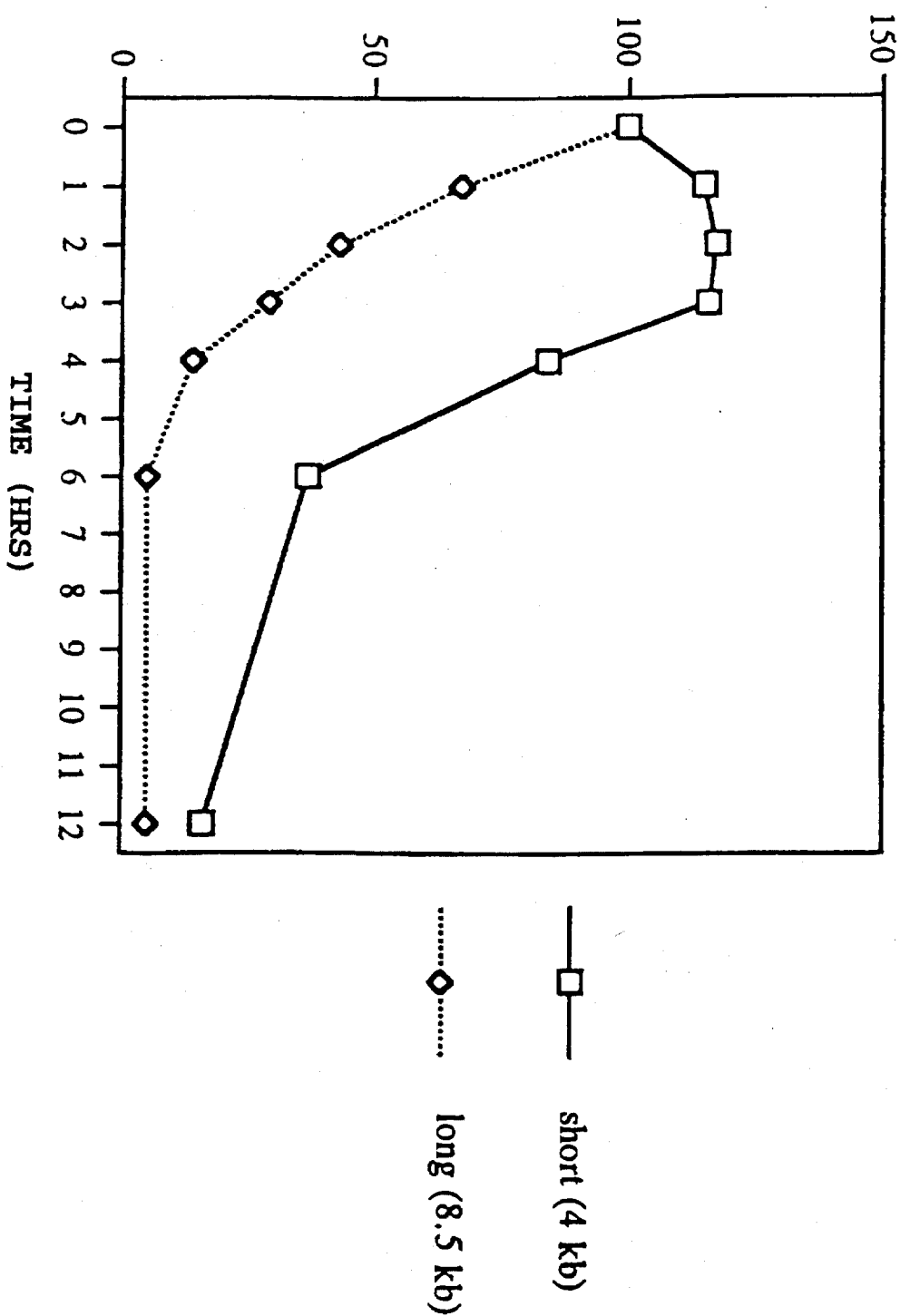
FIG. 2 is a line graph showing a time course of PKCα mRNA levels in cells (shown as percent of control) after treatment with oligonucleotide 7911. Levels of both the short and long mRNA transcripts are indicated. Levels of short mRNA transcript are represented by solid lines. Levels of long mRNA transcript are represented by dotted lines. By 12 hours after treatment with ISIS 7911, levels of both messages were reduced by over 80%.

This invention provides nucleic acid sequences that encode portions of the 3' untranslated region of human PKCα. Polynucleotide probes and methods of detecting PKCα are also provided. In some embodiments of the present invention, nucleic acid sequences specific for a particular mRNA transcript of PKCα are provided, as well as polynucleotide probes and methods for specific detection of this transcript.

In accordance with other embodiments of the present invention, antisense oligonucleotides are provided that are specifically hybridizable with nucleic acids encoding PKCα. In still other embodiments, antisense oligonucleotides are provided which are specifically hybridizable with a particular mRNA transcript of PKCα. Such oligonucleotides may be conveniently and desirably presented in a pharmaceutically acceptable carrier.

In accordance with still other aspects of the invention are provided methods for modulating the expression of PKCα or of a particular PKCα mRNA transcript in cells. Additional aspects of the invention are directed to methods of detection in cells of nucleic acids that encode PKCα and specific detection in cells of nucleic acids that encode particular PKCα transcripts. Such methods comprise contacting the cells with oligonucleotides in accordance with the invention in order to interfere with the effect of or to detect said nucleic acid.

In still other embodiments of the invention are provided methods for treating animals having a disease associated with expression of PKCα or one of its transcripts. Such methods comprise contacting the animal with a therapeutically effective amount of oligonucleotides in accordance with the invention in order to modulate the expression of PKCα, to treat conditions associated with PKCα, or to effect a diagnosis thereof.

DETAILED DESCRIPTION OF THE INVENTION

The present invention provides diagnostics, therapeutics and research reagents useful to diagnose, treat and study conditions associated with PKCα. In accordance with the present invention a nucleic acid molecule having a sequence which encodes the 3' untranslated region of human PKCα is provided (FIG. 1). This sequence was determined from cDNA clones prepared from human A549 cells, beginning with a clone overlapping the 3'-most end of the previously published PKCα sequence [Finkenzeller et al., *Nucl. Acids Res.* 18:2183 (1990); Genbank accession number X52479] and extending in the 3' direction. A polyadenylation site which was reached after 1080 nucleotides (nucleotide 1136 in FIG. 1); has been identified as the 3' end of the short (4 kb) mRNA transcript of PKCα. An additional 676 nucleotides of sequence in the 3' direction were determined, which sequence is unique to the long (8kb) mRNA transcript of PKCα. The nucleic acid molecule of the present invention may preferably be comprised of deoxyribonucleic acids and may be double-stranded in some aspects of the present invention. Also in accordance with the present invention, said nucleic acid molecules are isolated. "Isolated" as the term is used herein, in meant to refer to molecules which have been purified or synthesized so as to be substantially homogenous. The term does not exclude the possibility that certain impurities may be present in the composition, but is, instead, meant to refer to the absence of non-relevant nucleic acid sequences.

In accordance with the present invention polynucleotide probes specifically hybridizable to a portion of the 3' untranslated region of the human PKCα gene are provided. Polynucleotide probes specifically hybridizable to a portion of the long mRNA transcript of PKCα are also provided. Such probes may be used for diagnostic or research purposes to detect or quantitate the expression of PKCα. Probes may be used to specifically detect or quantirate the long transcript of PKCα. Said polynucleotide probes may range in length from about 5 to about 50 nucleotide units. In more preferred embodiments of the present invention the probes may be from about 8 to about 30 nucleotide units in length. Ideally, said probes range in length from about 12 to about 25 nucleotide units. It is recognized that since polynucleotide probes of the present invention ideally do not exceed 50 nucleotides in length, said probes may specifically hybridize to only a portion of the targeted sequence. The portion of the PKCα sequence to be targeted can be identified by one skilled in the art. Most suitably, a target sequence is chosen which is unique, thereby decreasing background noise attributable to hybridization by the probe other than to the target. By way of example, one skilled in the art would be unlikely to select a repeating sequence of adenine nucleotide units as this is a common sequence occuring in many genes. The practitioner might choose to perform a search and comparison of sequences found in a Genebank in order to identify and design a useful probe. Such methods of conventionally used to identify unique sequences. These unique sequences, when used as probes, need not necessarily be crucial to the regulation of the expression of PKCα.

Oligonucleotides have recently become accepted as therapeutic moieties in the treatment of disease states in animals and man. For example, workers in the field have now identified antisense, triplex and other oligonucleotide therapeutic compositions which are capable of modulating expression of genes implicated in vital, fungal and metabolic diseases.

For example, U.S. Pat. No. 5,098,890 is directed to antisense oligonucleotide therapies for certain cancerous conditions. U.S. Pat. No. 5,135,917 provides antisense oligonucleotides that inhibit human interleukin-1 receptor expression. U.S. Pat. No. 5,087,617 provides methods for treating cancer patients with antisense oligonucleotides. U.S. Pat. No. 5,166,195 provides oligonucleotide inhibitors of HIV. U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenzavirus. U.S. Pat. No. 4,806,463 provides antisense oligonucleotides and methods using them to inhibit HTLV-III replication. Antisense oligonucleotides have been safely administered to humans and several clinical trials of antisense oligonucleotides are presently underway. It is, thus, established that oligonucleotides can be useful therapeutic instrumentalities and that the same can be configured to be useful in treatment regimes for treatment of cells and animals, especially humans.

Current agents which modulate the activity or metabolism of PKC exhibit many unacceptable side effects due to their lack of specificity, or they exhibit only limited effectiveness in inhibiting the enzyme. The instant invention circumvents problems encountered by prior workers by modulating the production of the enzyme, rather than inhibiting the enzyme directly, to achieve the therapeutic effect. In accordance with the present invention, oligonucleotides are provided which specifically hybridize with nucleic acids encoding the 3'UTR region of human PKCα. The oligonucleotides are designed to bind either directly to mRNA or to a selected DNA portion forming a triple stranded structure, thereby modulating the amount of mRNA made from the gene. In either case, expression of PKCα is ultimately modulated. "Hybridization," in the context of this invention, means hydrogen bonding, also known as Watson-Crick base pairing, between complementary bases, usually on opposite nucleic acid strands or two regions of a nucleic acid strand, to form a double-stranded duplex. Guanine and cytosine are examples of complementary bases which are known to form three hydrogen bonds between them. Adenine and thymine are examples of complementary bases which are known to form two hydrogen bonds between them. "Specifically hybridizable" and "substantially complementary" are terms which indicate a sufficient degree of complementarity to avoid non-specific binding of the oligonucleotide (or polynucleotide probe) to non-target sequences under conditions in which specific binding is desired, i.e., under physiological conditions in the case of in vivo assays and therapeutic treatment, or, in the case of in vitro assays, under conditions in which the assays are conducted. It is understood that an oligonucleotide or polynucleotide probe need not be 100% complementary to its target nucleic acid sequence to be specifically hybridizable.

The relationship between an oligonucleotide and its complementary (or "target") nucleic acid is commonly denoted as "antisense."

It is preferred to target specific genes for antisense attack. It has been discovered that the gene coding for PKCα is particularly useful for this approach. Inhibition of PKCα expression is expected to be useful for the treatment of diseases, particularly hyperproliferative and inflammatory disorders. However, "modulation" in the context of this invention means either an increase or decrease (stimulation or inhibition) of PKCα expression.

In the context of this invention, the term "oligonucleotide" refers to an oligomer or polymer of ribonucleic acid or deoxyribonucleic acid. This term includes oligomers consisting of naturally occurring bases, sugars and intersugar (backbone) linkages as well as oligomers having non-naturally occurring portions which function similarly. Such modified or substituted oligonucleotides are often preferred over native forms because of properties such as, for example, enhanced cellular uptake and increased stability in the presence of nucleases.

Specific examples of some preferred oligonucleotides envisioned for this invention may contain phosphorothioates, phosphotriesters, methyl phosphonates, short chain alkyl or cycloalkyl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Also preferred are oligonucleotides having morpholino backbone structures. Summerton, J. E. and Weller, D. D., U.S. Pat. No. 5,034,506. In other preferred embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, Science 1991, 254, 1497. Other preferred oligonucleotides may contain sugar moieties comprising one of the following at the 2' position: OH, SH, $SCH_3$, F, OCN, O($CH_2$)$_n$$NH_2$ or O($CH_2$)$_n$$CH_3$ where n is from 1 to about 10; $C_1$ to $C_{10}$ lower alkyl, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl;

heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group. Base modifications or "universal" bases such as inosine may also be included. Chimetic or "gapped" oligonucleotides are also preferred embodiments of the invention. These oligonucleotides contain two or more chemically distinct regions, each comprising at least one nucleotide. Typically, one or more region comprises modified nucleotides that confer one or more beneficial properties, for example, increased nuclease resistance, increased uptake into cells or increased binding affinity for the RNA target. One or more unmodified or differently modified regions retains the ability to direct RNase H cleavage. Chimeric oligonucleotides are disclosed in PCT application US92/11339 which is assigned to the assignee of the instant application and which is incorporated by reference herein in its entirety. Examples of chimetic oligonucleotides which are presently preferred are 2'-O-methyl or 2'-O-propyl oligonucleotides having a "deoxy gap" region of 2'-deoxynucleotides. Usually this deoxy gap region is located between the two 2'-alkyl regions. In these preferred embodiments, the internucleotide (backbone) linkages may be uniformly phosphorothioate or some combination of phosphorothioate and phosphodiester linkages.

All such oligonucleotides are best described as being functionally interchangeable with natural oligonucleotides (or synthesized oligonucleotides along natural lines), but having one or more differences from natural structure. All such oligonucleotides are encompassed by this invention so long as they function effectively to hybridize with the PKC RNA.

The oligonucleotides in accordance with this invention preferably comprise from about 5 to about 50 nucleotide units. It is more preferred that such oligonucleotides comprise from about 8 to 30 nucleotide units, and still more preferred to have from about 12 to 25 nucleotide units. As will be appreciated, a nucleotide unit is a base-sugar combination (or a combination of analogous structures) suitably bound to an adjacent nucleotide unit through phosphodiester or other bonds forming a backbone structure.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is also well known to use similar techniques to prepare other oligonucleotides such as phosphorothioates or alkylated derivatives. Other modified and substituted oligomers can be similarly synthesized.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. In a preferred embodiment, the oligonucleotide is specifically hybridizable with sequences in the 3'-untranslated region (3' UTR) of PKCα.

The oligonucleotides of this invention are designed to be hybridizable with messenger RNA derived from the PKCα gene. Such hybridization, when accomplished, interferes with the normal roles of the messenger RNA to cause a modulation of its function in the cell. The functions of messenger RNA to be interfered with may include all vital functions such as translocation of the RNA to the site for protein translation, actual translation of protein from the RNA, maturation of the RNA, splicing of the RNA to yield one or more mRNA species, and possibly even independent catalytic activity which may be engaged in by the RNA. The overall effect of such interference with the RNA function is to modulate expression of the PKCα gene.

The oligonucleotides and polynucleotides of this invention can be used in diagnostics, therapeutics, prophylaxis, and as research reagents and kits. Since the oligonucleotides and polynucleotides of this invention specifically hybridize to the PKCα gene and its mRNA, sandwich and other assays can easily be constructed to exploit this fact. Furthermore, since certain oligonucleotides and polynucleotides of this invention hybridize specifically to a particular mRNA transcript of PKCα, such assays can be devised for screening of cells and tissues for particular PKCα transcripts. Such assays can be utilized for diagnosis of diseases associated with various PKCα forms. Provision of means for detecting hybridization of polynucleotides with the PKC gene can routinely be accomplished. Such provision may include enzyme conjugation, radiolabelling or any other suitable detection systems. Kits for detecting the presence or absence of PKCα or a particular transcript thereof may also be prepared.

For therapeutic or prophylactic treatment, oligonucleotides are administered in accordance with this invention. Oligonucleotides may be formulated in a pharmaceutical composition, which may include carriers, thickeners, diluents, buffers, preservatives, surface active agents and the like in addition to the oligonucleotide. Pharmaceutical compositions may also include one or more active ingredients such as antimicrobial agents, antiinflammatory agents, anesthetics, and the like in addition to oligonucleotides.

The pharmaceutical composition may be administered in a number of ways depending on whether local or systemic treatment is desired, and on the area to be treated. Administration may be done topically (including ophthalmically, vaginally, rectally, intranasally), orally, by inhalation, or parenterally, for example by intravenous drip or subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms or gloves may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

The following examples illustrate the present invention and are not intended to limit the same.

EXAMPLES

Example 1

DNA Sequencing of the 3' Untranslated Region of Human PKCα

A549 cells (obtained from the American Type Culture Collection, Bethesda Md.) were grown to confluence in 6-well plates (Falcon Labware, Lincoln Park, N.J.) in Dulbecco's modified Eagle's medium (DME) containing 1 g glucose/liter and 10% fetal calf serum (FCS, Irvine Scientific, Santa Ana, Calif.). Cells were harvested and total RNA was isolated using standard methods. Sambrook, J., Fritsch, E., and T. Maniatis (1989). Molecular Cloning: a laboratory manual. Cold Spring Harbor Laboratory, Cold Spring Harbor, N.Y., Ch. 7).

cDNA was made from the RNA using the 3' RACE technique of Frohman et al. [Frohman, M. A., Dush, M. K. and G. R. Martin (1988) Proc. Natl. Acad. Sci. U.S.A. 85:8998–9002] and the 3' RACE kit from Gibco/BRL (Bethesda, Md.). For making the first strand of cDNA, an oligo dT primer was used. For subsequent amplification from the site of the poly(A) tail, the oligonucleotide provided in the kit or an identical oligonucleotide (ISIS 5586; SEQ ID NO: 4: 5'-GGCCACGCGTCGACTAGTACTTT TTTTTTTTTTTTT-3'). For amplification from the interior of the known sequence, ISIS 6288 was used (SEQ ID NO: 5: 5'-GGGGTAGAATGCGGCGGCAGTATGAAACTC ACCAGCG-3')- The DNA resulting from the PCR reaction was gel-purified, digested with Sal I and Bcl I, and then cloned into the Bluescript plasmid (Stratagens, La Jolla, Calif.) using standard techniques (Sambrook et al., 1989). The cloned DNA was sequenced using a Sequenase Kit from USB.

The new sequence obtained, from the Bcl I site near the 3' end of the previously known sequence (GenBank accession number x52479) to the most frequently obtained site of polyadenylation is shown as nucleotides 56-1136 in FIG. 1. This site is believed to be the 3' end of the short (4kb) PKCα message.

To extend this sequence and hence obtain sequences specific for the long PKCα message (8.5 kb), the technique of Inverse PCR was performed. Ochman, H., Gerber, A. S. and D. L. Hartl (1988) Genetics 120:621–623. This technique was performed three times using a three sets of primers and restriction enzymes. Each round resulted in about 200 bases of new sequence; the total of the new sequence (SEQ ID NO: 1) is shown in bold type (nucleotides 1137–1812) in FIG. 1. This sequence is shown extending in the 3' direction beginning at the Bcl I site (TGATCA) near the end of the previously published PKCα cDNA sequence. Finkenzeller et al., Nucl. Acids Res. 18:2183 (1990); Genbank accession number X52479. Newly determined sequences begin at nucleotide 56 and are underlined (SEQ ID NO:2). The most common site of polyadenylation, believed to be the 3' end of the short (4 kb) mRNA transcript, is at nucleotide 1136. Sequences downstream from this site, and therefore unique to the long message, are in bold (SEQ ID NO:3).

Example 2

Oligonucleotide Synthesis

Unmodified DNA oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2M solution of 3H-1,2-benzodithiole-3-one 1,1-dioxide in acetonitrile for the stepwise thiation of the phosphite linkages. The thiation cycle wait step was increased to 68 seconds and was followed by the capping step.

2'-O-methyl phosphorothioate oligonucleotides are synthesized according to the procedures set forth above substituting 2'-O-methyl β-cyanoethyldiisopropyl phosphoramidites (Chemgenes, Needham, Mass.) for standard phosphoramidites and increasing the wait cycle after the pulse delivery of tetrazole and base to 360 seconds. Similarly, 2'-O-propyl phosphorothioate oligonucleotides may be prepared by slight modifications of this procedure.

After cleavage from the controlled pore glass column (Applied Biosystems) and deblocking in concentrated ammonium hydroxide at 55° C. for 18 hours, the oligonucleotides were purified by precipitation twice out of 0.5M NaCl with 2.5 volumes ethanol. Analytical gel electrophoresis was accomplished in 20% acrylamide, 8M urea, 45 mM Tris-borate buffer, Ph 7.0.

Example 3

Antisense Oligonucleotides Targeted to Novel Sequences in the 3' UTR of PKCα

A series of phosphorothioate antisense oligonucleotides, complementary to the novel sequence obtained as described in Example 1, were designed and synthesized. These oligonucleotides were screened on the basis of their ability to cause the reduction or elimination of PKCα RNA in A549 cells 24 hours after the start of treatment. A549 cells were treated with phosphorothioate oligonucleotides at 500 nM for four hours in the presence of the cationic lipids DOTMA/DOPE, washed and allowed to recover for an additional 20 hours. Total RNA was extracted and 20μg of each was resolved on 1.2% gels and transferred to nylon membranes. These blots were probed with a $^{32}$P radiolabeled PKC-α cDNA probe and then stripped and reprobed with a radiolabeled G3PDH probe to confirm equal RNA loading. The two major PKC-α transcripts (8.5 kb and 4.0 kb) were examined and quantified with a PhosphorImager (Molecular Dynamics, Sunnyvale Calif.). The oligonucleotides and their activities are shown in Table 1.

TABLE 1

Inhibition of PKCα mRNA (both long and short) by
phosphorothioate antisense oligonucleotides (500 nM)
Expressed as percent of control mRNA level

| ISIS# | Sequence | Activity | Target region | SEQ ID NO: |
|---|---|---|---|---|
| 7416 | CAGTGCCCATGTGCAGGGAG | 100% | PKCα long mRNA | 6 |
| 7417 | AGAACCTGCACAAATAGAGC | 100% | PKCα long mRNA | 7 |
| 7418 | AGAAACAAGAACCTGCACAA | 100% | PKCα long mRNA | 8 |
| 7419 | GCAAGGGATTCAGCTAAAAC | 100% | PKCα long mRNA | 9 |
| 7420 | AGGGAGGGAAAGCACAGAAG | 100% | PKCα long mRNA | 10 |
| 7902 | AGGGAGGGAAAGCACAGAAG | 90% | PKCα long mRNA | 11 |
| 7907 | TCAGCTCAAAAATAGTCCTC | 85% | PKCα long mRNA | 12 |
| 7908 | CGAAAGGTGACATGAAGAAA | 100% | PKCα long mRNA | 13 |
| 7909 | GGCGGAGGAACCAGGACGAA | 90% | PKCα long mRNA | 14 |
| 7911 | GCAATGCCACGTGTGTACCA | 50% | PKCα long mRNA | 15 |
| 7912 | TGCAAAACGTATTAAAATCC | 100% | PKCα short mRNA | 16 |
| 7913 | TTATAAACATGCAAAATTCA | 100% | PKCα short mRNA | 17 |

ISIS 7911 (SEQ ID NO: 15) reduced PKCα mRNA levels (both long and short messages) in this preliminary experiment by 50% compared to control. This oligonucleotide is therefore preferred. Further analysis demonstrated that ISIS 7911 selectively reduced the amount of long (8.5 kb) message during the first six hours of treatment, with a fourfold selectivity at 3 hours post-treatment. By 12 hours after treatment with ISIS 7911, levels of both messages were reduced by over 80%. Time-course data are shown in FIG. 2.

What is claimed is:

1. An antisense oligonucleotide 20 to 25 nucleotides in length, wherein said oligonucleotide comprises a contiguous nucleotide sequence selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 and SEQ ID NO: 17.

2. An antisense oligonucleotide 20 to 25 nucleotides in length, wherein said oligonucleotide comprises a contiguous nucleotide sequence selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 and SEQ ID NO: 15.

3. An antisense oligonucleotide 20 to 25 nucleotides in length, wherein said oligonucleotide comprises a contiguous nucleotide sequence set forth in SEQ ID NO: 15.

4. An antisense oligonucleotide, wherein said oligonucleotide consists of 12–19 consecutive nucleotides of any sequence selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 and SEQ ID NO: 17.

5. An antisense oligonucleotide, wherein said oligonucleotide consists of 12–19 consecutive nucleotides of any sequence selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 and SEQ ID NO: 15.

6. An antisense oligonucleotide, wherein said oligonucleotide consists of 12–19 consecutive nucleotides set forth in SEQ ID NO: 15.

7. A composition comprising the antisense oligonucleotide of any one of claims 1–6 and a pharmaceutically acceptable carrier.

8. A composition comprising the antisense oligonucleotide of claim 6 and a pharmaceutically acceptable carrier.

9. A method of reducing the expression of protein kinase C alpha in a cell in vitro comprising contacting the cell with an antisense oligonucleotide 20 to 25 nucleotides in length, wherein said oligonucleotide comprises a contiguous nucleotide sequence selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 and SEQ ID NO: 17, wherein said oligonucleotide reduces the expression of protein kinase C alpha in said cell.

10. A method of reducing the expression of protein kinase C alpha in a cell in vitro comprising contacting the cell with an antisense oligonucleotide 20 to 25 nucleotides in length, wherein said oligonucleotide comprises a contiguous nucleotide sequence selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 and SEQ ID NO: 15, wherein said oligonucleotide reduces the expression of protein kinase C alpha in said cell.

11. A method of reducing the expression of protein kinase C alpha in a cell in vitro comprising contacting the cell with an antisense oligonucleotide 20 to 25 nucleotides in length, wherein said oligonucleotide comprises a contiguous nucleotide sequence set forth in SEQ ID NO: 15, wherein said oligonucleotide reduces the expression of protein kinase C alpha in said cell.

12. A method of reducing the expression of protein kinase C alpha in a cell in vitro comprising contacting the cell with an antisense oligonucleotide consisting of 12 to 19 consecutive nucleotides in length of any sequence selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17, wherein said oligonucleotide reduces the expression of protein kinase C alpha in said cell.

13. A method of reducing the expression of protein kinase C alpha in a cell in vitro comprising contacting the cell with an antisense oligonucleotide consisting of 12 to 19 consecutive nucleotides in length of any sequence selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 and SEQ ID NO: 15, wherein said oligonucleotide reduces the expression of protein kinase C alpha in said cell.

14. A method of reducing the expression of protein kinase C alpha in a cell in vitro comprising contacting the cell with an antisense oligonucleotide consisting of 12 to 19 consecutive nucleotides in length set forth in SEQ ID NO: 15, wherein said oligonucleotide reduces the expression of protein kinase C alpha in said cell.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 1812 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
TGATCAACTG TTCAGGGTCT CTCTCTTACA ACCAAGAACA TTATCTTAGT GGAAGATGGT      60

ACGTCATGCT CAGTGTCCAG TTTAATTCTG TAGAAGTTAC GTCTGGCTCT AGGTTAACCC     120

TTCCTAGAAA GCAAGCAGAC TGTTGCCCCA TTTTGGGTAC AATTTGATAT ACTTTCCATA     180

CCCTCCATCT GTGGATTTTT CAGCATTGGA ATCCCCCAAC CAGAGATGTT AAAGTGAGCT     240

GTCCCAGGAA ACATCTCCAC CCAAGACGTC TTTGGAATCC AAGAACAGGA AGCCAAGAGA     300

GTGAGCAGGG AGGGATTGGG GGTGGGGGGA GGCCTCAAAA TACCGACTGC GTCCATTCTC     360

TGCCTCCATG GAAACAGCCC CTAGAATCTG AAAGGCCGGG ATAAACCTAA TCACTGTTCC     420

CAAACATTGA CAAATCCTAA CCCAACCATG GTCCAGCAGT TACCAGTTTA AACAAAAAAA     480

ACCTCAGATG AGTGTTGGGT GAATCTGTCA TCTGGTACCC TCCTTGGTTG ATAACTGTCT     540

TGATACTTTT CATTCTTTGT AAGAGGCCAA ATCGTCTAAG GACGTTGCTG AACAAGCGTG     600

TGAAATCATT TCAGATCAAG GATAAGCCAG TGTGTACATA TGTTCATTTT AATCTCTGGG     660

AGATTATTTT TCCATCCAGG GTGCCATCAG TAATCATGCC ACTACTCACC AGTGTTGTTC     720

GCCAACACCC ACCCCACAC ACACCAACAT TTGCTGCCT ACCTTGTTAT CCTTCTCAAG       780

AAGCTGAAGT GTACGCCCTC TCCCTTTTG TGCTTATTTA TTTAATAGGC TGCAGTGTCG      840
```

| | | | | | | |
|---|---|---|---|---|---|---|
| CTTATGAAAG | TACGATGTAC | AGTAACTTAA | TGGAAGTGCT | GACTCTAGCA | TCAGCCTCTA | 900 |
| CCGATTGATT | TTCCTCCCTT | CTCTAGCCCT | GGATGTCCAC | TTAGGGATAA | AAAGAATATG | 960 |
| GTTTGGTTC | CCATTTCTAG | TTCACGTTGA | ATGACAGGCC | TGGAGCTGTA | GAATCAGGAA | 1020 |
| ACCCGGATGC | CTAACAGCTC | AAAGATGTTT | TGTTAATAGA | AGGATTTTAA | TACGTTTTGC | 1080 |
| AAATGCATCA | TGCAATGAAT | TTTGCATGTT | TATAATAAAC | CTTAATAACA | AGTGAATAGA | 1140 |
| AGGATTTTAA | TACGTTTTGC | AAATGCATCA | TGCAATGAAT | TTTGCATGTT | TATAATAAAC | 1200 |
| CTTAATAACA | AGTGAATCTA | TATTATTGAT | ATAATCGTAT | CAAGTATAAA | GAGAGTATTA | 1260 |
| TAATAATTTT | ATAAGACACA | ATTGTGCTCT | ATTTGTGCAG | GTTCTTGTTT | CTAATCCTCT | 1320 |
| TTTCTAATTA | AGTTTTAGCT | GAATCCCTTG | CTTCTGTGCT | TTCCCTCCCT | GCACATGGGC | 1380 |
| ACTGTATCAG | ATAGATTACT | TTTTAAATGT | AGATAAAATT | TCAAAAATGA | ATGGCTAGTT | 1440 |
| TACGTGATAG | ATTAGGCTCT | TACTACATAT | GTGTGTGTAT | ATATATGTAT | TTGATTCTAC | 1500 |
| CTGCAAACAA | ATTTTATTG | GTGAGGACTA | TTTTTGAGCT | GACACTCCCT | CTTAGTTTCT | 1560 |
| TCATGTCACC | TTTCGTCCTG | GTTCCTCCGC | CACTCTTCCT | CTTGGGACA | ACAGGAAGTG | 1620 |
| TCTGATTCCA | GTCTGGCCTA | GTACGTTGGT | ACACACGTGG | CATTGCGCAG | CACCTGGGCT | 1680 |
| GACCTTTGTG | TGTAGCGTGT | GTGTGTGTTT | CCTTCTTCCC | TTCAGCCTGT | GACTGTTGCT | 1740 |
| GACTCCAGGG | GTGGGAGGGA | TGGGGAGACT | CCCCTCTTGC | TGTGTGTACT | GGACACGCAG | 1800 |
| GAAGCATGCT | GA | | | | | 1812 |

( 2 ) INFORMATION FOR SEQ ID NO:2:

( i ) SEQUENCE CHARACTERISTICS:
        ( A ) LENGTH: 1757 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

| | | | | | | |
|---|---|---|---|---|---|---|
| ATGGTACGTC | ATGCTCAGTG | TCCAGTTTAA | TTCTGTAGAA | GTTACGTCTG | GCTCTAGGTT | 60 |
| AACCCTTCCT | AGAAAGCAAG | CAGACTGTTG | CCCCATTTTG | GGTACAATTT | GATATACTTT | 120 |
| CCATACCCTC | CATCTGTGGA | TTTTTCAGCA | TTGGAATCCC | CCAACCAGAG | ATGTTAAAGT | 180 |
| GAGCTGTCCC | AGGAAACATC | TCCACCCAAG | ACGTCTTTGG | AATCCAAGAA | CAGGAAGCCA | 240 |
| AGAGAGTGAG | CAGGGAGGGA | TTGGGGGTGG | GGGAGGCCT | CAAAATACCG | ACTGCGTCCA | 300 |
| TTCTCTGCCT | CCATGGAAAC | AGCCCCTAGA | ATCTGAAAGG | CCGGGATAAA | CCTAATCACT | 360 |
| GTTCCCAAAC | ATTGACAAAT | CCTAACCCAA | CCATGGTCCA | GCAGTTACCA | GTTAAACAA | 420 |
| AAAAAACCTC | AGATGAGTGT | TGGGTGAATC | TGTCATCTGG | TACCCTCCTT | GGTTGATAAC | 480 |
| TGTCTTGATA | CTTTCATTC | TTTGTAAGAG | GCCAAATCGT | CTAAGGACGT | TGCTGAACAA | 540 |
| GCGTGTGAAA | TCATTTCAGA | TCAAGGATAA | GCCAGTGTGT | ACATATGTTC | ATTTAATCT | 600 |
| CTGGGAGATT | ATTTTCCAT | CCAGGGTGCC | ATCAGTAATC | ATGCCACTAC | TCACCAGTGT | 660 |
| TGTTCGCCAA | CACCCACCCC | CACACACACC | AACATTTGC | TGCCTACCTT | GTTATCCTTC | 720 |
| TCAAGAAGCT | GAAGTGTACG | CCCTCTCCCC | TTTTGTGCTT | ATTTATTTAA | TAGGCTGCAG | 780 |
| TGTCGCTTAT | GAAAGTACGA | TGTACAGTAA | CTTAATGGAA | GTGCTGACTC | TAGCATCAGC | 840 |
| CTCTACCGAT | TGATTTTCCT | CCCTTCTCTA | GCCCTGGATG | TCCACTTAGG | GATAAAAAGA | 900 |
| ATATGGTTTT | GGTTCCCATT | TCTAGTTCAC | GTTGAATGAC | AGGCCTGGAG | CTGTAGAATC | 960 |
| AGGAAACCCG | GATGCCTAAC | AGCTCAAAGA | TGTTTTGTTA | ATAGAAGGAT | TTAATACGT | 1020 |

-continued

| | | | | | |
|---|---|---|---|---|---|
| TTTGCAAATG | CATCATGCAA | TGAATTTTGC | ATGTTTATAA | TAAACCTTAA | TAACAAGTGA | 1080
| ATAGAAGGAT | TTTAATACGT | TTTGCAAATG | CATCATGCAA | TGAATTTTGC | ATGTTTATAA | 1140
| TAAACCTTAA | TAACAAGTGA | ATCTATATTA | TTGATATAAT | CGTATCAAGT | ATAAAGAGAG | 1200
| TATTATAATA | ATTTATAAG | ACACAATTGT | GCTCTATTTG | TGCAGGTTCT | TGTTCTAAT | 1260
| CCTCTTTTCT | AATTAAGTTT | TAGCTGAATC | CCTTGCTTCT | GTGCTTTCCC | TCCTGCACA | 1320
| TGGGCACTGT | ATCAGATAGA | TTACTTTTA | AATGTAGATA | AAATTTCAAA | AATGAATGGC | 1380
| TAGTTTACGT | GATAGATTAG | GCTCTTACTA | CATATGTGTG | TGTATATATA | TGTATTTGAT | 1440
| TCTACCTGCA | AACAAATTTT | TATTGGTGAG | GACTATTTTT | GAGCTGACAC | TCCCTCTTAG | 1500
| TTTCTTCATG | TCACCTTTCG | TCCTGGTTCC | TCCGCCACTC | TTCCTCTTGG | GGACAACAGG | 1560
| AAGTGTCTGA | TTCCAGTCTG | GCCTAGTACG | TTGGTACACA | CGTGGCATTG | CGCAGCACCT | 1620
| GGGCTGACCT | TTGTGTGTAG | CGTGTGTGTG | TGTTCCTTC | TTCCCTTCAG | CCTGTGACTG | 1680
| TTGCTGACTC | CAGGGGTGGG | AGGGATGGGG | AGACTCCCCT | CTTGCTGTGT | GTACTGGACA | 1740
| CGCAGGAAGC | ATGCTGA | | | | | 1757

( 2 ) INFORMATION FOR SEQ ID NO:3:

( i ) SEQUENCE CHARACTERISTICS:
        ( A ) LENGTH: 676 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

| | | | | | |
|---|---|---|---|---|---|
| TAGAAGGATT | TTAATACGTT | TTGCAAATGC | ATCATGCAAT | GAATTTTGCA | TGTTTATAAT | 60
| AAACCTTAAT | AACAAGTGAA | TCTATATTAT | TGATATAATC | GTATCAAGTA | TAAAGAGAGT | 120
| ATTATAATAA | TTTTATAAGA | CACAATTGTG | CTCTATTTGT | GCAGGTTCTT | GTTCTAATC | 180
| CTCTTTTCTA | ATTAAGTTTT | AGCTGAATCC | CTTGCTTCTG | TGCTTTCCCT | CCCTGCACAT | 240
| GGGCACTGTA | TCAGATAGAT | TACTTTTAA | ATGTAGATAA | AATTTCAAAA | ATGAATGGCT | 300
| AGTTTACGTG | ATAGATTAGG | CTCTTACTAC | ATATGTGTGT | GTATATATAT | GTATTTGATT | 360
| CTACCTGCAA | ACAAATTTT | ATTGGTGAGG | ACTATTTTG | AGCTGACACT | CCCTCTTAGT | 420
| TTCTTCATGT | CACCTTTCGT | CCTGGTTCCT | CCGCCACTCT | TCCTCTTGGG | GACAACAGGA | 480
| AGTGTCTGAT | TCCAGTCTGG | CCTAGTACGT | TGGTACACAC | GTGGCATTGC | GCAGCACCTG | 540
| GGCTGACCTT | TGTGTGTAGC | GTGTGTGTGT | GTTCCTTCT | TCCCTTCAGC | CTGTGACTGT | 600
| TGCTGACTCC | AGGGGTGGGA | GGGATGGGGA | GACTCCCCTC | TTGCTGTGTG | TACTGGACAC | 660
| GCAGGAAGCA | TGCTGA | | | | | 676

( 2 ) INFORMATION FOR SEQ ID NO: 4:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( i v ) ANTI-SENSE: no ( x i ) SEQUENCE DESCRIPTION: SEQ ID NO: 4:

GGCCACGCGT CGACTAGTAC TTTTTTTTT TTTTTT     37

( 2 ) INFORMATION FOR SEQ ID NO: 5:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( i v ) ANTI-SENSE: no ( x i ) SEQUENCE DESCRIPTION: SEQ ID NO: 5:

GGGGTAGAAT GCGGCGGCAG TATGAAACTC ACCAGCG                     37

( 2 ) INFORMATION FOR SEQ ID NO: 6:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 6:

CAGTGCCCAT GTGCAGGGAG                                   20

( 2 ) INFORMATION FOR SEQ ID NO: 7:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 7:

AGAACCTGCA CAAATAGAGC                                   20

( 2 ) INFORMATION FOR SEQ ID NO: 8:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 8:

AGAAACAAGA ACCTGCACAA                                   20

( 2 ) INFORMATION FOR SEQ ID NO: 9:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 9:

GCAAGGGATT CAGCTAAAAC                                   20

( 2 ) INFORMATION FOR SEQ ID NO: 10:

( i ) SEQUENCE CHARACTERISTICS:
        ( A ) LENGTH: 20
        ( B ) TYPE: nucleic acid ( C ) STRANDEDNESS: single
( D ) TOPOLOGY: linear ( i v ) ANTI-SENSE: yes ( x i ) SEQUENCE DESCRIPTION: SEQ ID NO: 10:

AGGGAGGGAA AGCACAGAAG        20

( 2 ) INFORMATION FOR SEQ ID NO: 11:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 11:

AGGGAGGGAA AGCACAGAAG        20

( 2 ) INFORMATION FOR SEQ ID NO: 12:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 12:

TCAGCTCAAA AATAGTCCTC        20

( 2 ) INFORMATION FOR SEQ ID NO: 13:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 13:

CGAAAGGTGA CATGAAGAAA        20

( 2 ) INFORMATION FOR SEQ ID NO: 14:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 14:

GGCGGAGGAA CCAGGACGAA        20

( 2 ) INFORMATION FOR SEQ ID NO: 15:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 15:

GCAATGCCAC GTGTGTACCA 20

( 2 ) INFORMATION FOR SEQ ID NO: 16:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 16:

TGCAAAACGT ATTAAAATCC 20

( 2 ) INFORMATION FOR SEQ ID NO: 17:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 17:

TTATAAACAT GCAAAATTCA 20